(12) United States Patent
Capriotti et al.

(10) Patent No.: US 10,398,725 B2
(45) Date of Patent: *Sep. 3, 2019

(54) OPHTHALMIC COMPOSITIONS AND METHODS OF USE

(71) Applicant: Veloce BioPharma, LLC, Fort Lauderdale, FL (US)

(72) Inventors: Joseph Capriotti, Christiansted, VI (US); Kara Capriotti, Fort Washington, PA (US); Jesse Pelletier, Miami, FL (US); Kevin Stewart, Christiansted, VI (US)

(73) Assignee: Veloce BioPharma, LLC, Fort Lauderdale, FL (US)

( * ) Notice: Subject to any disclaimer, the term of this patent is extended or adjusted under 35 U.S.C. 154(b) by 23 days.

This patent is subject to a terminal disclaimer.

(21) Appl. No.: 15/667,033

(22) Filed: Aug. 2, 2017

(65) Prior Publication Data

US 2018/0021371 A1 Jan. 25, 2018

Related U.S. Application Data

(63) Continuation of application No. 15/200,960, filed on Jul. 1, 2016, now Pat. No. 9,770,466.

(60) Provisional application No. 62/187,973, filed on Jul. 2, 2015.

(51) Int. Cl.
| | | |
|---|---|---|
| A61K 31/79 | (2006.01) | |
| A61K 33/18 | (2006.01) | |
| A61K 47/38 | (2006.01) | |
| A61K 9/00 | (2006.01) | |
| A61K 9/06 | (2006.01) | |
| A61K 47/20 | (2006.01) | |

(52) U.S. Cl.
CPC ............ *A61K 31/79* (2013.01); *A61K 9/0048* (2013.01); *A61K 9/06* (2013.01); *A61K 33/18* (2013.01); *A61K 47/20* (2013.01); *A61K 47/38* (2013.01)

(58) Field of Classification Search
None
See application file for complete search history.

(56) References Cited

U.S. PATENT DOCUMENTS

| | | |
|---|---|---|
| 5,126,127 A | 6/1992 | Bhagwat et al. |
| 2004/0220264 A1 | 11/2004 | Yu et al. |
| 2005/0196418 A1 | 9/2005 | Yu et al. |
| 2017/0000819 A1 | 1/2017 | Capriotti et al. |

FOREIGN PATENT DOCUMENTS

WO WO 2012-154740 A1 11/2012

OTHER PUBLICATIONS

Pelletier, J. S., et al., Rosacea Blepharoconjunctivitis Treated with a Novel Preparation of Dilute Povidone Iodine and Dimethylsulfoxide: a Case Reprort and Revieew of the Lieterature, Ophthalmol Ther., online publication Nov. 15, 2015 at Springelink.com, DOI 10.1007/s40123-015-0040-4.

*Primary Examiner* — Bethany P Barham
*Assistant Examiner* — Barbara S Frazier
(74) *Attorney, Agent, or Firm* — Studebaker & Brackett PC

(57) ABSTRACT

Described are stable topical formulations useful in the treatment of viral infection, demodex infection and bacterial infection of the eye, and methods of using the compositions for treating viral infection, demodex infection and bacterial infection of the eye.

19 Claims, No Drawings

OPHTHALMIC COMPOSITIONS AND METHODS OF USE

CROSS-REFERENCE TO RELATED APPLICATIONS

This application is a continuation of U.S. patent application Ser. No. 15/200,960, filed Jul. 1, 2016, which claims the benefit of U.S. Provisional Application, Ser. No. 62/187,973, filed Jul. 2, 2015.

BACKGROUND OF THE INVENTION

Millions of human patients suffer from viral infection or viral wart infection, demodex infection, fungal or yeast infection, or bacterial infection of the skin, including skin of the eye, eyelid or periocular region.

Infections of the eye or eyelid may occur via direct person-to-person skin contact, or indirectly through contaminated surfaces in a publicly accessed area, such as a public swimming pool or gymnasium. Exposure to the infectious agent can occur through minor abrasions and infection is promoted via maceration of the epithelia. Autoinoculation is common as well.

Verruca vulgaris, the medical term for wart, serves as an umbrella term for all warts. Warts can result from viral infections that are most often associated with Human Papilloma Virus (HPV) or Molluscum Contagiosum Virus (WV) Non-genital varieties of skin warts occur in 20% of schoolchildren with equal frequency in both sexes.

Viral or viral wart infection, demodex infection, fungal or yeast infection, or bacterial infection of the eyelids, conjunctiva, cornea, ocular surface or Meibomian glands, can manifest as blepharitis and/or blepharoconjunctivitis or conjunctivitis—an infectious and inflammatory condition of the eyelid or ocular surface.

Blepharoconjunctivitis and blepharitis are commonly encountered conditions affecting approximately 15% of the population, and represent an inflammatory, infectiouis or mixe condition of the eyelids. Blepharitis may involve the dermis, eyelashes, tarsal conjunctiva, mucocutaneous junction or meibomian glands and is most often caused by gram positive bacterial infection, such as *Stapylococcus, Corynebacterium*, and *Pripionibacterium* species. However, other agents causing blepharitis include viral, demodex (mite), or yeast infections, seborrhea, rosacea, and hormonal dysregulation.

Left untreated, blepharitis may cause dry eye exacerbation, loss of cilia, corneal ulceration, and impart increased risk of endophthalmitis after cataract surgery. For facility in understanding, it is commonly compartmentalized into inflammation affecting the structures of the anterior, posterior lid margin or both.

Anterior blepharitis most commonly presents as anterior lid and lash crusting with or without the presence of collarettes. Other manifesations may also include skin or lash flaking associated with seborrhea or angular inflammation particular to *Moraxella* or virus.

Posterior blepharitis is also commonly referred to as meibomian gland disease. Meibomian glands are responsible for the release of lipids into the tear film, effectively mitigating evaporative tear loss. Besides the chronic irritation, inflammation and erythema common to all blepharitis, the posterior variant may further be characterized by inspissation of the meibomian glands, keratinization of orifices, telangiectasia, and posterior margin lid thickening. Bacterial lipases stemming from the ocular flora may also act upon meibomian secretions creating free fatty acids which further disturb the ocular surface.

Current treatments for bacterial, demodex, fungal/yeast, and viral infections, including warts and ophthalmic conditions such as blepharitis, can be ineffective in that they treat only a subset of the causative agent of the infection. Many of the current treatments incorporate undesirable ingredients, such as steroids or other potentially harmful components.

A recent discovery by Capriotti, et al., has disclosed compositions comprising an iodophor such as povidone-iodine (PVP-I), as an active ingredient, and dimethyl sulfoxide (DMSO) were shown to be useful for treating fungal infections of the skin and nails. See, e.g., US Publication No. US2014/0205559 (Capriotti '559), which is incorporated herein by reference in its entirety.

Although a variety of organic solvents, including dimethyl sulfoxide (DMSO), are known to enhance the percutaneous absorption of certain medicaments, it has been long-accepted in the pharmaceutical arts that DMSO enhances penetration for small molecules or low molecular weight (LMW) compounds or drugs, only, and was not expected to enhance penetration of high molecular weight (HMW) compounds greater than about 10,000 Daltons, such as polymers, e.g., povidone-iodine. DMSO has only recently, and unexpectedly, been demonstrated to enhance penetration of povidone-iodine (PVP-I). PVP-I preparations range in molecular weights from 1,000 to 1,000,000 or more. Topical pharmaceutical compositions have been approved using only PVP grades K29-32. One acceptable PVP grade is PVP K30, which has a MW of 30,000 to 60,000 daltons (average MW of about 40,000 daltons). Accordingly, prior to the teachings of Capriotti '559, one skilled in the art would not employ DMSO in a topical pharmaceutical composition to enhance skin penetration of large molecules, polymers or high-molecular weight substances such as PVP-I.

Moreover, DMSO was understood and accepted in the art to be toxic to the eye and was not considered to be an acceptable ingredient in a composition intended for topical administration to the eye or periocular region. Therefore, not only was DMSO generally recognized as being unacceptable for use as a penetration enhancer for high molecular weight polymeric compounds, such as povidone-iodine, DMSO was particularly avoided as an ingredient for use in ophthalmic preparations, and especially avoided as an ingredient for topical ophthalmic preparations.

Further, although gel formulations comprising povidone-iodine and DMSO were mentioned, generally, in Capriotti '559 and related publications, it was discovered that certain formulations comprising povidone-iodine, DMSO, and a gelling agent were not stable for a sufficient period of time to provide a viable pharmaceutical product having an acceptable shelf-life. Only when particular amounts of povidone-iodine were combined with particular amounts of DMSO and particular amounts of gelling agent was stability observed to be sufficient to provide a viable pharmaceutically acceptable product having an acceptable and approvable shelf-life.

Therefore, it was previously unknown that topical ophthalmic gel formulations comprising povidone-iodine (PVP-I) and DMSO, with a gelling agent, could be made having pharmaceutically acceptable properties and utility. Specifically, the subject topical ophthalmic formulation comprises DMSO, which has heretofore not been used for ophthalmic preparations due to the expected toxicity of DMSO to the eye.

Neither were ophthalmic preparations known to contain above 2.0% gelling agent, such as hydroxyethylcellulose (HEC). The subject formulation is therefore unexpectedly effective and stable, making it useful in treating certain viral, demodex, fungal/yeast, or bacterial infections manifesting as ophthalmic conditions (e.g., blepharitis, blepharoconjunctivitis, viral conjunctivitis, bacterial conjunctivitis, keratitis, or the like.)

Thus, the current invention is a significant advance in the art, and discloses the surprising and unexpected discovery that a topical gel composition comprising particular ingredients, namely, PVP-I, DMSO, and a gelling agent, in particular concentration combinations, can provide advantageous and unexpected results in the treatment of infection of the eye such as blepharitis or other eye conditions.

SUMMARY OF THE INVENTION

The present invention concerns a topical gel composition comprising an iodophor, a penetration enhancer, and a gelling agent, wherein the composition is particularly effective in treating viral, demodex, fungal/yeast, or bacterial infection that can cause warts or eye conditions, such as blepharitis. Thus, the subject invention further comprises a method of treating viral, demodex, fungal/yeast, or bacterial infection using a topical gel composition as disclosed herein. The composition can further comprise optional pharmaceutically acceptable excipients or solvents or co-solvents.

A composition of the subject invention preferably comprises active pharmaceutical ingredient (API) approved by the United States Food and Drug Administration (FDA) as acceptable for use in a pharmaceutical preparation. A preferred composition of the invention further comprises inactive ingredients or excipients that are FDA-approved for topical administration. An FDA-approved API or inactive ingredient or excipient is referred to herein as "pharmaceutically acceptable." Accordingly, a topical composition, formulation, or preparation of the subject invention comprising a pharmaceutically acceptable API, inactive ingredient or excipient is referred to herein as a "pharmaceutically acceptable" topical composition.

Similarly, an ophthalmic composition of the subject invention comprising FDA-approved active or inactive ingredients acceptable for use in an ophthalmic preparation, is referred to herein as a "pharmaceutically acceptable ophthalmic composition," or "ophthalmically acceptable" composition, and comprises an API, an excipient, or a solvent which is "pharmaceutically acceptable" for ophthalmic use.

More particularly, the subject invention relates to a stable topical composition comprising an iodophor having a molecular weight of greater than 10,000 Daltons, e.g. povidone-iodine, such as povidone-iodine K30, dimethyl sulfoxide (DMSO), and a gelling agent, and optional additional pharmaceutically or ophthalmically acceptable excipients or solvents or co-solvents.

A composition of the subject invention can be useful in a method for treating viral infection or viral wart infection, demodex infection, fungal or yeast infection, or bacterial infection of the eye, eyelids, conjunctiva, cornea, ocular surface, Meibomian glands, or periocular region.

A topical gel composition of the subject invention is unexpectedly highly stable at room temperature in the presence of aqueous or anhydrous ingredients.

A topical ophthalmic gel composition of the subject invention can comprise about 0.1% to about 1.5% povidone-iodine (PVP-I); about 30% to about 99% dimethyl sulfoxide (DMSO); and about 1% to about 10% gelling agent. The topical gel composition of the invention unexpectedly exhibits greater efficacy in treating skin infection or blepharitis, compared to a liquid composition substantially free of a gelling agent and comprising about 0.1% to about 1.5% povidone-iodine and about 30% to about 99% DMSO.

A preferred topical ophthalmic gel composition comprises about 0.15% to 1.5% povidone-iodine (PVP-I). A more preferred composition can comprise about 0.25% PVP-I to 0.5% PVP-I. The FDA has approved the topical use of PVP-I having a MW which averages 40,000. Accordingly, a PVP-I grade of K30 is preferred for use in the subject composition.

A preferred topical ophthalmic gel composition comprises about 30% to about 99% DMSO. A more preferred composition can comprise about 30% to about 70% DMSO. A most referred composition of the invention comprises about 40% to about 49% DMSO, and even more preferably, about 44% DMSO.

A preferred topical ophthalmic gel composition comprises about 2% to about 5% gelling agent. A more preferred composition can comprise about 3% gelling agent.

A particularly useful topical ophthalmic gel composition which has been prepared for testing comprises 0.25% PVP-I; 44% DMSO; 3% hydroxyethylcellulose; and aqueous solvent, q.s. 100%. A preferred aqueous solvent is water or aqueous isotonic solution.

A gelling agent useful for preparing a topical ophthalmic gel composition of the invention can include, as is well known in the art, gum, agar, carrageenan, petrolatum, or a cellulosic polymer or the like. One preferred cellulosic polymer useful as a gelling agent is hydroxyethyl cellulose. An alternative cellulosic polymer gelling agent is hydroxymethyl cellulose.

A topical ophthalmic gel composition of the invention preferably comprises povidone-iodine, or PVP-I having an average molecular weight greater than 10,000. More preferably, the composition of the invention comprises PVP-I having an average molecular weight between about 20,000 to about 1,000,000. One preferred embodiment comprises PVP-I having an average molecular weight between about 30,000 to about 60,000, or greater. Each of the PVP-I ingredients referred to herein means a "high molecular weight PVP-I," or "HMW PVP-I."

The topical ophthalmic gel composition is ophthalmically acceptable, comprising one or more ophthalmically acceptable ingredients. The ophthalmic gel composition embodiments described herein can advantageously can exhibit greater efficacy in treating infectious conditions of the eye or eyelid, compared to a liquid composition substantially free of a gelling agent (or a gelling agent at concentrations below those required for forming a gel) and comprising about 0.1% to about 10% povidone-iodine and about 30% to about 99% DMSO.

A most preferred topical ophthalmic gel composition comprises a pharmaceutical grade povidone-iodine at a range of 0.15% to 0.5%; greater than 30% DMSO up to 90% DMSO; and a gelling agent at a range of 2.5% to 5%. All percentages are w/w unless otherwise specified. This most preferred composition can also include a co-solvent, such as polyethylene glycol (PEG). This most preferred composition is unexpectedly stable and efficacious for treating certain eye infections.

A preferred embodiment of the composition comprises a solution, and more particularly, a gel solution, wherein the povidone-iodine is dissolved or solubilized in the final composition. Preferably, the subject composition is not an emulsion or suspension of particulates of ingredients in the gel or final composition.

Preferred embodiments of a topical gel composition of the invention are free of any additional API or anti-inflammatory drug, such as a steroid, e.g., corticosteroid, or non-steroidal anti-inflammatory drug (NSAID). Thus, a composition of the invention can be described as steroid-free, NSAID-free, steroid-free and NSAID-free, or anti-inflammatory-free. A composition of the invention is advantageously useful for treatment of the described ophthalmic conditions without an anti-inflammatory, without a steroid, or without an NSAID present in the composition.

One preferred embodiment of a composition of the invention is a stable ophthalmically acceptable gel composition comprising
  0.15% to 1.5% povidone-iodine (PVP-I);
  30% to 97% dimethyl suifoxide (DMSO);
  2.5% to 5% hydroxyethylcellulose; and
  water or isotonic co-solvent;
wherein, the composition is formulated as a topical ophthalmic gel, free of additional anti-inflammatory drug, or anti-inflammatory-free.

One preferred embodiment of a composition of the invention is a stable, ophthalmically acceptable gel composition comprising
  0.15% to 1.5% povidone-iodine (PVP-I);
  30% to 97% dimethyl sulfoxide (DMSO);
  2.5% to 5% hydroxyethylcellulose; and
  water or isotonic co-solvent;
wherein, the composition is formulated as a topical ophthalmic gel, free of steroid.

One preferred embodiment of a composition of the invention is a stable, ophthalmically acceptable gel composition comprising
  0.15% to 1.5% povidone-iodine (PVP-I);
  30% to 97% dimethyl sulfoxide (DMSO);
  2.5% to 5% hydroxyethylcellulose; and
  water or isotonic co-solvent;
wherein, the composition is formulated as a topical ophthalmic gel, free of corticosteroid.

One preferred embodiment of a composition of the invention is a stable, ophthalmically acceptable gel composition comprising
  0.15% to 1.5% povidone-iodine (PVP-I);
  30% to 97% dimethyl sulfoxide (DMSO);
  2.5% to 5% hydroxyethylcellulose; and
  water or isotonic co-solvent;
wherein, the composition is formulated as a topical ophthalmic gel, free of NSAID.

A method according to the subject invention comprises, generally, one or more as-needed topical administrations or topical applications of a topical ophthalmic gel composition of the invention, namely, a topical composition comprising an iodophor, DMSO, and a gelling agent, to the site, until the ophthalmic infection is eliminated, or is substantially inhibited. In a preferred method, the subject gel composition is administered directly to the site of the infection as needed (PRN), preferably at least once per day (QD), or more preferably at least two times per day (BID) until results are seen, typically for about one week, up to about 24 weeks. Advantageously, the composition of the subject invention can be administered directly to the eye or periocular region and presents no toxicity to the eye.

A preferred embodiment of the invention comprises a method of treating an infectious condition of the eye or eyelid, comprising applying an effective amount of a stable, topical ophthalmic gel composition to a site of the infection to reduce or eliminate the infection.

The method of the invention can be useful in treating blepharitis, conjunctivitis, corneal ulcer, HSV keratitis, conjunctival neoplasia, AC inflammation, post-operative endophthalmitis, and endophthalmitis after intravitreal or intracameral injection, which is caused by or associated with one or more infectious agents such as bacteria, demodex, fungus or yeast, or virus.

DETAILED DESCRIPTION OF THE INVENTION

The present invention concerns a topical gel composition comprising an antiseptic agent, a penetration enhancer, and a gelling agent. Preferably, the composition comprises povidone-iodine as the antiseptic agent, dimethylsulfoxide (DMSO) as the penetration enhancer, and a cellulosic gelling agent, such as hydroxyethylcelluose (HEC). The composition can, optionally, further comprise a lubricant or co-solvent, or other pharmaceutically or ophthalmically acceptable excipients. For example, a composition for treating an ophthalmic condition, such as blepharitis can include an ophthalmically acceptable excipient.

The subject composition is surprisingly useful for the treatment of viral, demodex, fungal/yeast or bacterial infection of the eye, eyelids, conjunctiva, cornea, ocular surface and Meibomian glands, which can cause blepharitis.

A specific but non-limiting example of a formulation of the invention providing a useful pharmaceutical preparation comprises solid PVP-I dissolved in DMSO with one or additional co-solvents in solution and prepared as a gel or semi-solid.

In another embodiment, DMSO can be added to aqueous solutions of PVP-I. In an example, DMSO can be present as a co-solvent with water in the range of 10%-99%. One embodiment of such a formulation can include a range of excipients such as water, or sodium chloride, sodium dihydrogen phosphate monohydrate, disodium hydrogen phosphate anhydrous and water, as well as other aqueous solutions or isotonic buffers known to those skilled in the art.

Percentages set forth herein are (w/w), with respect to the specified component in the overall composition, unless otherwise indicated. For example, a composition comprising 1% PVP-I and 45% DMSO has 1% PVP-I by weight, with respect to the total composition.

In an embodiment, a composition comprises povidone-iodine in the range of about 0.01% to about 15%. In another embodiment, a composition comprises povidone-iodine in the range between 0.05% and 12.5%. In another embodiment, a composition comprises povidone-iodine in the range between 0.05% and 10.0%. In another embodiment, a composition comprises povidone-iodine in the range between 0.1% and 10.0%. In another embodiment, a composition comprises povidone-iodine in the range between 0.1% and 1.0%. In another embodiment, a composition comprises povidone-iodine in the range between 0.15% and 1.5 5%. In another embodiment, a composition comprises povidone-iodine in the range between 0.25% and 0.5%.

In an embodiment, a composition comprises povidone-iodine of about 0.01%, about 0.05%, about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1.00%, about 1.1%, about 1.2%, about 1.3%, about 1.4%, about 1.5%, or any range determinable from the preceding percentages. All percentages are expresses as w/w unless otherwise specified.

In an embodiment, a composition comprises DMSO and PVP-I. In an embodiment, a composition consists essentially of DMSO and PVP-I and a gelling agent in an aqueous or anhydrous diluent. In an embodiment, a composition consists of DMSO and PVP-I and a gelling agent and a co-solvent in an aqueous or anhydrous diluent. In an embodiment, a composition is anhydrous. In an embodiment, a composition is substantially anhydrous. In an embodiment, a composition comprises a measurable amount of water.

In an embodiment, DMSO, e.g., anhydrous DMSO, is used in a composition. In an embodiment, substantially anhydrous DMSO is used in a composition. It will be understood by one of skill in the art that DMSO can be produced and/or obtained in differing grades, and that one of the variables among DMSO preparations of different grades is the water content. By way of example, DMSO may be completely anhydrous (also referred to herein simply as "anhydrous"), substantially anhydrous, or may contain water to a measurable degree. It will be understood that the amount of measurable water in a DMSO preparation may vary based on limitations of the instrumentation and techniques used to make such measurements.

In an embodiment, DMSO that is not completely anhydrous may be substantially anhydrous and contain water at a level below levels of detectability. In an embodiment, DMSO that is not completely anhydrous may contain water, wherein the water content is about at least 0.01%, about at least 0.02%, about at least 0.03%, about at least 0.04%, about at least 0.05%, about at least 0.06%, about at least 0.07%, about at least 0.08%, about at least 0.09%, about at least 0.1%, about at least 0.2%, about at least 0.3%, about at least 0.4%, about at least 0.5%, about at least 0.6%, about at least 0.7%, about at least 0.8%, about at least 0.9%, about at least 1.0%, about at least 1.5%, about at least 2.0%, about at least 2.5%, about at least 5%, about at least 7.5%, about at least 10%, about at least 12.5%, or greater. It will be understood that DMSO may contain one or more other impurities in addition to water.

In an embodiment, a composition comprises at least one of United States Pharmacopeial Convention (USP) grade DMSO, Active Pharmaceutical Ingredient (API) grade DMSO, analytical grade DMSO, and American Chemical Society (ACS) Spectrophotometric grade DMSO. In an embodiment, a composition comprises DMSO having <0.1% water by KF titration and >99.9% determined on an anhydrous basis.

As set forth above, the percent amount of DMSO in a composition is described in a weight-to-weight (w/w) ratio with respect to one or more other components of the composition, unless otherwise indicated. In an embodiment, the weight percent DMSO is the balance of the weight percent after addition of PVP-I. By way of a non-limiting example, a composition may comprise 1 weight percent (1%) PVP-I and 99 weight percent (99%) DMSO. It will be understood that in the foregoing example, the DMSO component of the composition may be completely anhydrous, substantially anhydrous, or may contain water to a measurable degree. In an embodiment, the weight percent DMSO is the balance of the weight percent after addition of PVP-I and any other components (e.g., co-solvent, water, additional active ingredient, etc.). In an embodiment, the weight percent DMSO is the balance of the weight percent after addition of iodophor and other components, if any. In an embodiment, the weight percent penetrant in a composition is the balance of the weight percent after addition of iodophor and other components, if any.

In an embodiment, a composition comprises DMSO in the range of 30% to 99.99%. In an embodiment, a composition comprises DMSO in the range of 35% to 99.99%. In another embodiment, a composition comprises DMSO in the range of 40% and 99.9%. In another embodiment, a composition comprises DMSO in the range of 30% and 97%. In another embodiment, a composition comprises DMSO in the range of 35% and 75%. In another embodiment, a composition comprises DMSO in the range of 40% and 50%. In another embodiment, a composition comprises DMSO in the range of 40% and 49%. In another embodiment, a composition comprises DMSO in the range of 43% and 45%. In another embodiment, a composition comprises DMSO at 44%.

In an embodiment, a composition comprises gelling agent in the range of greater than 2%. In an embodiment, a composition comprises gelling agent in the range of 2.1% to 10%. In another embodiment, a composition comprises gelling agent in the range of 2.5% and. 5.0%. In another embodiment, a composition comprises gelling agent in the range of 2.5% and 4%. In another embodiment, a composition comprises about 2.5% to about 3.5% gelling agent. In another embodiment, a composition comprises 3% gelling agent.

In an embodiment, a composition comprises a co-solvent in the range of 1% to 99.99%. In another embodiment, a composition comprises a co-solvent n the range of 5% and 99.9%. In another embodiment, a composition comprises a co-solvent in the range of 10% and 99.9%. In another embodiment, a. composition comprises a co-solvent in the range of 20% and 99.9%. In another embodiment, a composition comprises a co-solvent in the range of 30% and 99.9%. In another embodiment, a composition comprises a co-solvent in the range of 40% and 99.9%. In another embodiment, a composition comprises a co-solvent n the range of 50% and 99.9%. In another embodiment, a composition comprises a co-solvent in the range of 60% and 99.9%. In another embodiment, a composition comprises a co-solvent in the range of 70% and 99.9%. In another embodiment, a composition comprises a co-solvent in the range of 80% and 99.9%, and in yet another embodiment, between 90% and 99.9%.

In an embodiment, a composition comprises a co-solvent at about 1%. In other embodiments, a composition comprises a co-solvent at about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%.

Examples of co-solvents include, but are not limited to, alcohols, silicones, polyethylene glycol, propylene glycol, glycerin, petrolatum, hydroxymethylcellulose, methylcellulose, and combinations thereof. In an embodiment, a co-solvent is polyethylene glycol.

In an embodiment, a composition comprises DMSO in the range of about 0.01% to 99.99% and further comprises at least one penetrant in the range of 0.01% to about 99.99%. In an embodiment, a composition comprises DMSO and further comprises at least one penetrant in the range of about 0.1% to about 50%. In another embodiment, a composition comprises DMSO and further comprises at least one penetrant in the range between about 5% and about 50%. In another embodiment, a composition comprises DMSO and further comprises at least one penetrant in the range between about 10% and about 99%. In an embodiment, a composition comprises DMSO, at least one co-solvent, and at least one penetrant. In an embodiment, a co-solvent is also a penetrant.

In an embodiment, where possible, compositions may include pharmaceutically acceptable salts of compounds in the composition. In an embodiment, compositions comprise acid addition salts of the present compounds. In an embodiment, compositions comprise base addition salts of the present compounds. As used herein, the term pharmaceutically acceptable salts or complexes refers to salts or complexes (e.g., solvates, polymorphs) that retain the desired biological activity of the parent compound and exhibit minimal, if any, undesired toxicological effects.

In various embodiments, the compositions encompassed herein comprise pharmaceutically acceptable excipients such as those listed in REMINGTON: THE SCIENCE AND PRACTICE OF PHARMACY 866-885 (Alfonso R. Gennaro ed. 19th ed. 1995; Ghosh, T. K.; et al. TRANSDERMAL AND TOPICAL DRUG DELIVERY SYSTEMS (1997), hereby incorporated herein by reference, including, but not limited to, protectives, adsorbents, demulcents, emollients, preservatives, antioxidants, moisturizers, buffering agents, solubilizing agents, skin-penetration agents, and surfactants.

Protectives and adsorbents include, but are not limited to, dusting powders, zinc sterate, collodion, dimethicone, silicones, zinc carbonate, aloe vera gel and other aloe products, vitamin E oil, allantoin, glycerin, petrolatum, and zinc oxide.

Demulcents include, but are not limited to, benzoin, hydroxypropyl cellulose, hydroxypropyl methylcellulose, and polyvinyl alcohol.

Emollients include, but are not limited to, animal and vegetable fats and oils, myristyl alcohol, alum, and aluminum acetate.

Preservatives include, but are not limited to, chlorine dioxide, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable solubilizing agents include, but are not limited to, quaternary ammonium chlorides, cyclodextrins, benzyl benzoate, lecithin, and polysorbates.

Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methylpyrrolidone.

In an embodiment, a composition comprises PVP-I, DMSO, and polyethylene glycol and a gelling agent. In an embodiment, a composition comprises 0.25% PVP-I, 44% DMSO, 10% polyethylene glycol and 3% gelling agent. In an embodiment, the composition is substantially anhydrous. In an embodiment, a composition comprises PVP-I, DMSO, hydroxyethylcellulose, propylene glycol and glycerin. In an embodiment, a composition comprises 2% PVP-I, about 40% DMSO, and 10-33% propylene glycol and at least one additional inactive ingredient.

In one embodiment, the composition includes 0.15-0.5% PVP-I, 40-49% DMSO, 8-15% alcohol, 18-25% polyethylene glycol, 2.5-5.0% gelling agents, and 0-3% water. In one embodiment, the composition includes aprotic solvents. In one embodiment, the composition includes 0.15-0.5% PVP-I, 40-45% DMSO, 10-35% polyethylene glycol, 2.5-3.5% gelling agents, and 0-3% water. In one embodiment, the composition includes aprotic solvents.

In one embodiment, the invention comprises DMSO 40-50% (w/w), 0.25%-0.55% PVP-I (w/w) and hydroxypropyl methylcellulose or hydroxymethyl cellulose or hydroxyethyl cellulose.

In one embodiment, the composition is a solution and can be formulated as a semi-solid, e.g., a gel, ointment or cream; tincture; foam; aerosol or another common pharmaceutical dosage form. In one embodiment, the composition is a 0.25% PVP-I/44% DMSO solution dissolved in 3% gel, such as hydroxyethyl cellulose.

Stability

A. Visible Loss of Chromophore

Topical ophthalmic compositions comprising variations of the amounts and combinations of povidone-iodine, DMSO, and gelling agent ingredients were prepared to demonstrate the unpredictability of the stability for the subject compositions.

Compositions that are highly unstable, and are thus not suitable or useful as a topical ophthalmic preparation, will lose color and appear colorless within about 72 hours of making the preparation. The colorless state is a result of loss of titratable iodine compared with the amount of iodine in the povidone-iodine starting material. No further confirmatory testing of titratable iodine is needed for compositions that are colorless within 72 hours of preparation.

Compositions were prepared with 0.15%, 0.25%, and 0.5% povidone-iodine. For these compositions, DMSO was provided in amounts of 0% or in an amount of 30% to 90%. Specific compositions comprising DMSO were prepared comprising 44% DMSO. Gelling agent was provided in amounts of 0%, 0.5%. 1.0%, 1.5%, 2,5% or 3.0%.

All of the prepared compositions comprising aqueous PVP-I only and water, and 0% DMSO and 0% gelling agent were colorless within 72 hours and were not stable.

For preparations comprising 0.15% povidone-iodine and DMSO within the range of 30% to 90%, the compositions retained color and were stable when the gelling agent was provided at 3%. Long-term stability of the compositions which retained color for 72 hours or longer was confirmed by USP assay for titratable iodine compared to povidone-iodine starting material. The stable compositions of the subject invention retained at least 85% of titratable iodine in the povidone-iodine starting material for up to 18 months.

For preparations comprising 0.25% povidone-iodine and DMSO within the range of 30% to 90%, the compositions retained color and were stable when the amount of gelling agent was greater than or equal to 2.5%. Long-term stability of the compositions which retained color for 72 hours or longer was confirmed by USP assay for titratable iodine compared to povidone-iodine starting material. The stable compositions of the subject nvention retained at least 85% of titratable iodine in the povidone-iodine starting material for up to 18 months.

For preparations comprising 0.5% povidone-iodine and DMSO within the range of 30% to 90%, the compositions retained color and were stable when the amount of gelling agent was greater than or equal to 2.5%. Long-term stability of the compositions which retained color for 72 hours or longer was confirmed by USP assay for titratable iodine compared to povidone-iodine starting material. The stable compositions of the subject invention retained at least 85% of titratable iodine in the povidone-iodine starting material for up to 18 months.

These experimental results demonstrate that stability of the specific combination of ingredients, and within specific range amounts, namely, 0.15% to 0.5% povidone-iodine; 30% to 90% DMSO, and 2.5% to 5% gelling agent, are stable whereas compositions which deviate from these specific ingredients in specific range amounts are unstable, A preferred gelling agent is a cellulosic polymer, such as hydroxyethyl cellulose (HEC), hydroxymethyl cellulose (HMC), hydroxypropyl methylcellulose (HPMC), and the like. A most preferred gelling agent is hydroxyethyl cellulose (HEC).

A table showing results of the above-described experiments using selected compositions is provided in Table 1, below:

TABLE 1

Aqueous Research Formulations with Varying Amounts of PVP-I, DMSO, and Gelling Agent

| Formulation ID # | PVP-I (w/w) | DMSO (w/w) | HEC Gel (w/w) | Initial Color | 72 hrs. | 3 mos. | 6 mos. | 12 mos. | 18 mos. |
|---|---|---|---|---|---|---|---|---|---|
| #A4430 | 0.25 | 44% | 3% | Faint Yellow | Faint Yellow-unchanged; Titratable iodine, via USP method->85% | Faint Yellow-unchanged; Titratable iodine, via USP method->85% | Faint Yellow-unchanged; Titratable iodine, via USP method->85% | Faint Yellow-unchanged; Titratable iodine, via USP method->85% | Faint Yellow-unchanged; Titratable iodine, via USP method->85% |
| #A0000 | 0.25 | 0.0% | 0.0% | Faint yellow | colorless | NA | NA | NA | NA |
| #A4400 | 0.25 | 44% | 0.0% | Faint yellow | colorless | NA | NA | NA | NA |
| #A4405 | 0.25 | 44% | 0.5% | Faint yellow | colorless | NA | NA | NA | NA |
| #A0005 | 0.25 | 0.0% | 0.5% | Faint yellow | colorless | NA | NA | NA | NA |
| #A4410 | 0.25 | 44% | 1.0% | Faint yellow | colorless | NA | NA | NA | NA |
| #A0015 | 0.25 | 0.0% | 1.5% | Faint yellow | colorless | NA | NA | NA | NA |
| #B4430 | 0.5 | 44% | 3.0% | Medium yellow | Med Yellow-unchanged; Titratable iodine, via USP method->85% | Med Yellow-unchanged; Titratable iodine, via USP method->85% | Med Yellow-unchanged; Titratable iodine, via USP method->85% | Med Yellow-unchanged; Titratable iodine, via USP method->85% | Med Yellow-unchanged; Titratable iodine, via USP method->85% |
| #B0000 | 0.5 | 0.0% | 0.0% | Medium Yellow | colorless | NA | NA | NA | NA |
| #B4400 | 0.5 | 44% | 0.0% | Medium yellow | colorless | NA | NA | NA | NA |
| #B0005 | 0.5 | 0.0% | 0.5% | Medium yellow | colorless | NA | NA | NA | NA |
| #B0020 | 0.5 | 0.0% | 1.5% | Medium yellow | colorless | NA | NA | NA | NA |
| #C4430 | 0.15 | 44% | 3.0% | Faint yellow | Faint yellow-unchanged; Titratable iodine, via USP method->85% | Faint yellow-unchanged; Titratable iodine, via USP method->85% | Faint yellow-unchanged; Titratable iodine, via USP method->85% | Faint yellow-unchanged; Titratable iodine, via USP method->85% | Faint yellow-unchanged; Titratable iodine, via USP method->85% |
| #C0000 | 0.15 | 0.0% | 0.0% | Faint yellow | colorless | NA | NA | NA | NA |

TABLE 1-continued

Aqueous Research Formulations with Varying Amounts of PVP-I, DMSO, and Gelling Agent

| Formulation ID # | PVP-I (w/w) | DMSO (w/w) | HEC Gel (w/w) | Initial Color | 72 hrs. | 3 mos. | 6 mos. | 12 mos. | 18 mos. |
|---|---|---|---|---|---|---|---|---|---|
| #C4400 | 0.15 | 44% | 0.0% | Faint yellow | colorless | NA | NA | NA | NA |
| #C4405 | 0.15 | 44% | 0.5% | Faint yellow | colorless | NA | NA | NA | NA |
| #C4410 | 0.15 | 44% | 1.5% | Faint yelow | colorless | NA | NA | NA | NA |

In one embodiment, the formulations are stable at room temperature 25° C. for at least 6 months, 12 months, 18 months and 24 months. Stability is defined as where the final PVP-I concentration is at least 85%-120%, according to the LISP titration method for povidone-iodine, of the labeled concentration.

In one embodiment, the formulations are stable at temperature 2-8° C. for at least 6 months, 12 months, 18 months and 24 months. Stability is defined as where the final PVP-I concentration is at least 85%-120%, according to the USP method of the labeled concentration (e.g. if the label is 2% PVP-I providing for 0.2% iodine, therefore 90% would be 0.18 elemental iodine).

In one embodiment, the formulations are stable at room temperature −10 to −25° C. for at least 6 months, 12 months, 18 months and 24 months. Stability is defined as where the final PVP-I concentration is at least 85%-120%, according to the USP method of the labeled concentration (e.g. if the label is 2% PVP-I providing for 0.2% iodine, therefore 90% would be 0.18 elemental iodine).

In one embodiment, the formulations are stable at room temperature 15-30° C. for at least 6 months, 12 months, 18 months and 24 months. Stability is defined as where the final PVP-I concentration is at least 85%-120%, according to the USP method, of the labeled concentration (e.g. if the label is 2% PVP-I providing for 0.2% iodine, therefore 90% would be 0.18 elemental iodine).

In one embodiment, the formulations are stable at room temperature 40° C. for at least 1 months, 3 months, 6 months, 12 months, 18 months and 24 months. Stability is defined as where the final PVP-I concentration is at least 85%-120%, according to the USP method of the labeled concentration (e.g. if the label is 2% PVP-I providing for 0.2% iodine, therefore 90% would be 0.18 elemental iodine).

Methods of Preparation and Use

It is known to one of skill in the art that PVP-I aqueous solutions are difficult to stabilize at low PVP-I concentrations over a long period of time. By way of a non-limiting example, at concentrations of PVP-I less than about 0.6% (w/w, aqueous), PVP-I aqueous solutions rapidly decay to yield complex mixtures of iodinated and iodine-free constituents.

As described herein, it was surprisingly found that in the aprotic DMSO solvent system encompassed by the disclosure set forth herein, PVP-I gel solutions as low as 0.15% can be easily prepared and maintained as stable compositions for long periods of time. Also as described herein, hydrated DMSO solutions prepared from aqueous PVP-I and sufficient (about 3% or greater) gelling agent, demonstrate increased stability for the PVP-I component over at least 12 months at room temperature.

In an embodiment, a composition comprises dry, solid or powdered PVP-I dissolved or suspended in a composition comprising or consisting of DMSO. In another embodiment, DMSO is added to an aqueous preparation comprising or consisting of PVP-I.

Based on the disclosure herein, one of ordinary skill in the art will understand how to prepare a composition to arrive at the desired amounts of iodine, iodophor, and DMSO, among other possible components of the composition encompassed herein, without undue experimentation.

By way of a non-limiting example, a therapeutically-effective pharmaceutical composition is prepared using solid PVP-I, which is dissolved or suspended in DMSO. In an aspect, the composition is anhydrous. In an aspect, the composition is substantially anhydrous. In another embodiment, DMSO can be added to aqueous solutions of PVP-I to prepare a therapeutically-effective pharmaceutical composition. In an embodiment, DMSO is used in the range of 30%-99% as a co-solvent with water and other non-aqueous co-solvents. In an embodiment, a formulation includes one or more excipients. By way of a non-limiting example, excipients include, but are not limited to, sodium chloride, sodium dihydrogen phosphate monohydrate, disodium hydrogen phosphate anhydrous and water, as well as others known to those skilled in the art.

In an embodiment, a composition is prepared by adding PVP-I (w/v, aqueous) to pure DMSO q.s. to yield a resulting solution of 0.15-1.5% PVP-I (w/w) with DMSO. In another embodiment, compositions are prepared by dissolving solid PVP-I in pure DMSO q.s to obtain any of 0.1%, 0.2%, 0.25%, 0.3%, 0.35%, 0.4%, 0.45%, or 0.5% PVP-I (w/w) compositions, with DMSO as the solvent. In yet another embodiment, compositions are prepared by dissolving solid PVP-I in pure DMSO q.s to obtain any composition set forth, described, and/or encompassed herein. Similar compositions comprising aqueous PVP-I (with and without excipients commonly used and/or known in the art) and DMSO can be prepared from a stock 10% PVP-I aqueous solution and pure DMSO. Gelling agent can be added at an amount up to 5% (w/w) of the final concentration of the composition, preferably between about 2.0% and 5.0%, more preferably between about 2.5% and 5.0%, and most preferably about 3%.

It will be understood by the skilled artisan, however, that any starting composition of PVP-I, solid or liquid, may be used when the appropriate dilutions and adjustments are made to result in the desired final PVP-I concentration. Similarly, any starting composition of iodophor or elemental iodine may be used when the appropriate dilutions and adjustments are made to result in the desired final iodophor or elemental iodine concentration, respectively.

It will be understood, based on the disclosure set forth herein, in view of the skill in the art, that specific dosage for compounds and compositions encompassed herein may be determined empirically through clinical and/or pharmacokinetic experimentation, and that such dosages may be adjusted according to pre-specified effectiveness and/or toxicity criteria. It will also be understood that a specific dosage and treatment regimen for any particular patient will depend upon a variety of factors, including the activity of the specific compounds employed, the characteristics of the patient, drug combination, the judgment of the treating physician and the nature and severity of the particular disease or condition being treated.

In an embodiment, a therapeutic composition is prepared by optimizing one or more compounds for use in a dosage form different than that which is typically used for the compound. In an embodiment, a compound that is not typically administered in a topical dosage form is developed for use in a topical dosage form. The chemical and biological assays required for such development are known to one of skill in the art. The disclosure herein provides the skilled artisan with the guidance as to how to prepare such compounds and compositions comprising such compounds.

In an embodiment, a method of treating a subject having an ocular surface disease complicated by microbial colonization and/or infection includes administration of a composition set forth, described, and/or encompassed herein to treat the ocular surface disease, and the treatment of the ocular surface disease includes at least one of preventing or slowing the progression of the infection, preventing the spread of the infection, eradicating at least some of the infection, and eradicating the entire infection.

In an embodiment, a therapeutic composition is administered on a schedule once a day. In an embodiment, a therapeutic composition is administered twice a day. Typically, a gel composition of the subject invention can be administered as a ribbon having a length of about 1 cm to about 5 cm, up to 1 cm in diameter, onto the eye, under the eyelid, or at the periocular region of the eye to be treated.

In an embodiment, a therapeutic composition is administered three times a day, four times a day, five times a day, or more. In an embodiment, a therapeutic composition is administered less frequently than once a day. In an embodiment, a therapeutic composition is administered once every two days, once every three days, once every four days, once every five days, once every six days, or once every seven days. In an embodiment, a therapeutic composition is administered less frequently than once a week. In an embodiment, a therapeutic composition is administered once a month. In an embodiment, a therapeutic composition is administered twice a month.

In an embodiment, a therapeutic dosing regimen is continued for at least one day, at least two days, at least three days, at least four days, at least five days, at least six days, or at least seven days. In an embodiment, a therapeutic dosing regimen is continued for at least one week, at least two weeks, at least three weeks, at least four weeks, at least six weeks, at least eight weeks, at least ten weeks, at least twelve weeks, at least fourteen weeks, or at least sixteen weeks. In an embodiment, a therapeutic dosing regimen is continued for at least one month, at least two months, at least three months, at least four months, at least five months, at least six months, at least nine months, or at least twelve months.

The invention is further described by the following examples. In an aspect, the following examples demonstrate effective and/or successful treatment of the identified conditions using compositions and methods encompassed by the present disclosure. It should be recognized that variations based on the inventive features are within the skill of the ordinary artisan, and that the scope of the invention should not be limited by the examples. To properly determine the scope of the invention, an interested party should consider the claims herein, and any equivalent thereof. The entire disclosure of international patent applications, PCT/US2012/036942 and PCT/US2012/065298 are hereby incorporated herein by reference as if fully set forth herein. In addition, all citations herein are incorporated by reference, and unless otherwise expressly stated, all percentages are by weight/weight.

Additional examples of useful compositions described in this invention include the formulation of creams, petrolatum balms, salves, sprays, and other formulations well known to those in the art suitable for topical administration to the ocular surface or are "ophthalmically acceptable" compositions.

While the foregoing written description enables a person ordinarily skilled in the art to reproduce and use what is considered presently to be the best mode thereof, those of ordinary skill will understand and appreciate the existence of variations, combinations, derivatives, analogs and equivalents of the specific embodiments, methods and examples provided above. The invention should therefore not be limited by the above described embodiments, examples and methods by instead by all embodiments, examples and methods within the scope and spirit of the present invention.

Clinical Trial Results and Clinical Efficacy

In a 12-week clinical trial for treating blepharitis, the endpoint of complete eradication and/or the endpoint of substantial reduction in the signs and symptoms of blepharitis. The results from a randomized, controlled clinical trial demonstrates the effectiveness a formulation of the subject invention comprising up to 1-2% povidone-iodine, with a penetration enhancer, DMSO, which can successfully eliminate blepharitis. The blepharitis infections are assessed at 2-week intervals, with complete resolution demonstrated by the 12-week clinical assessment. By the end of a 12-week study complete resolution of signs and symptoms of blepharitis in at least 10%, at least 15%, at least 20%, at least 30% or at least 40% of study subjects is observed by the 12-week end-of-study visit.

In addition, a recent study of 18 patients showed that a gel formulation comprising 0.25% or 0.5% PVP-I gel formulation exhibits less irritation when administered to the Lower Lid Conjunctival Fornix. These results are summarized in Table 2, below:

TABLE 2

Ocular Irritation Study Using 0.25% PVP-I/DMSO (Dose "A") Gel or 0.5% PVP-I/DMSO (Dose "B") Gel In OD Lower Lid Conjunctival Fornix[1]

| Patient Number | Dose Applied | Discharge | Infection (redness) | Burning | Itch |
|---|---|---|---|---|---|
| 001 | A | 0 | 0 | 0 | 0 |
| 002 | A | 0 | 0 | 0 | 0 |
| 003 | A | 0 | 0 | 0 | 0 |
| 004 | A | 0 | 0 | 0 | 0 |
| 005 | A | 1 | 0 | 0 | 0 |
| 006 | A | 1 | 0 | 0 | 0 |
| 007 | A | 0 | 0 | 0 | 0 |
| 008 | A | 1 | 0 | 0 | 0 |

TABLE 2-continued

Ocular Irritation Study Using 0.25% PVP-I/DMSO
(Dose "A") Gel or 0.5% PVP-I/DMSO (Dose "B")
Gel In OD Lower Lid Conjunctival Fornix[1]

| Patient Number | Dose Applied | Discharge | Infection (redness) | Burning | Itch |
|---|---|---|---|---|---|
| 009 | A | 0 | 0 | 0 | 0 |
| 010 | A | 0 | 0 | 0 | 0 |
| 011 | A | 0 | 1 | 1 | 0 |
| 012 | A | 0 | 0 | 1 | 0 |
| 013 | B | 0 | 0 | 0 | 0 |
| 014 | B | 0 | 0 | 0 | 0 |
| 015 | B | 1 | 0 | 0 | 0 |
| 016 | B | 1 | 0 | 1 | 0 |
| 017 | B | 1 | 1 | 1 | 0 |
| 018 | B | 0 | 1 | 1 | 0 |

[1]All applications are ½" ribbon applied directly into lower lid conjunctival fornix; all grading for all signs and symptoms is 0-3 on a 4-point scale where 0 = absent, 1 = mild, 2 = moderate and 3 = severe.

In the examples from the clinical trials above, a liquid formulation was expected to provide adequate efficacy against warts and blepharitis. Most wart treatments are liquids. Surprisingly, it was found that a gel formulation provides unexpected advantages and increased efficacy compared with similar concentrations of PVP-I in a liquid formulation.

EXAMPLES

Example 1

Anterior Blepharitis; Treated with 1.0% PVP-I in 30% USP Grade DMSO with Polypropylene Glyclol and Hydroxymethylcellulose This patient was suffering from anterior blepharitis. In this common type of blepharitis, the anterior lid margin demonstrates madarosis, collarettes, scurf, lash debris and bacterial overgrowth. The lid margin may also be erythematous along with the conjunctiva and a decreased tear break up time is present. In this patient the condition had persisted for over 7 years and taken a chronic course. The patient had tried numerous antibiotics, steroids, lid scrubs, omega 3 fatty acids, and anti-inflamatories without benefit. Prepared was a composition as disclosed herein using 1.0% PVP-I in 30% DMSO with polypropylene glycol and hydroxymethylcellulose. The patient was treated by applying the solution topically to the eyelid and conjunctiva twice daily. Within one week, improvement was noted in and around the eyelid. After two weeks the condition rapidly improved, as the conjunctival erythema abated, tear break up time and dry eye symptoms normalized. Close inspection of the anterior lid eyelid margin revealed healthy cilia without associated debris or bacterial overgrowth.

Example 2

Posterior Blepharitis; Treated with 0.2% PVP-I in 35% % USP Grade DMSO with Hydroxyethyl Cellulose This patient was suffering from posterior blepharitis. In this most common type of blepharitis, the posterior lid margin demonstrates meibomian gland thickening, keratinization, fat saponification, and dilated, telangectatic lid vessels. The lid margin may also be erythematous along with the conjunctiva and decreased tear break up time is evident, In this patient the condition had persisted for over 7 years and taken a chronic course. The patient had tried numerous antibiotics, steroids, lid scrubs, omega 3 fatty acids and anti-inflammatories without benefit. Prepared was a composition as disclosed herein using 0.2% PVP-I in 35%% DMSO with hydroxyethyl cellulose. The patient was treated by applying the solution topically to the eyelid and conjunctiva twice daily. Within one week, improvement was noted in and around the eyelid. After two weeks the condition rapidly improved, as the conjunctival erythema abated, tear break up time and dry eye symptoms normalized. Close inspection of the posterior lid eyelid margin revealed healthy meibomian secretions, attenuation of posterior lid blood vessels and lack of erythema.

Example 3

A. Rosacea Blepharitis; Treated with 0.5% PVP-I in 38% USP Grade DMSO with Hydroxyethyl Cellulose This patient was suffering from Rosacea blepharitis. In this type of blepharitis, the posterior lid margin demonstrates meibomian gland thickening, keratinization, fat saponification, and dilated, telangectatic lid vessels. Anterior lid margin may also demonstrate scurf and bacterial overgrowth. The lid margin may also be erythematous along with the conjunctiva and a decreased tear break up time is present. In this patient the condition had persisted for over 7 years and taken a chronic course. The patient had tried numerous antibiotics, steroids, lid scrubs, omega 3 fatty acids and anti-inflammatories without benefit.

Prepared was a composition as disclosed herein using 0.5% PVP-I in 38% DMSO with hydroxyethyl cellulose. The patient was treated by applying the solution topically to the eyelid and conjunctiva twice daily. Within one week improvement was noted in and around the eyelid. After two weeks the condition rapidly improved, as the conjunctival erythema abated, tear break up time and dry eye symptoms normalized. The dilated, tortuous posterior lid margin vessels had significantly attenuated and meibomian secretions were healthy. Close inspection of the anterior lid eyelid margin revealed healthy cilia without associated debris or bacterial overgrowth.

B. Rosacea Blepharitis; Treated with 1% PVP-I in 44% USP Grade DMSO with 4% Hydroxyethylcellulose in Water A 78-year-old male with a past ocular history of glaucoma and pseudophakia presented with long standing ocular dryness, grittiness, periocular erythema and eyelid crusting. On facial inspection, nasal and facial telangiectasia with flushing were evident. His topical medical regimen included Latanoprost 1 drop QHS OU, Brimonidine 1 drop BID OU, and Dorzolamide/Timolol 1 drop BID OU. The patient endorsed utilization of a variety of medicines and treatments to abate this condition, however, they were of little benefit. Failed therapies included topical steroids, antibiotics including azithromycin, combination medicines, and cyclosporine. Oral medicines including doxycycline and DHA/ALA/EPA were also ineffective.

Slit lamp biomicroscopic examination revealed bilateral anterior lid margin erythema, crusting and thickening. Lash examination revealed some breakage with scurf-like deposition. Inspection of the posterior eyelids revealed inspissated meibomian glands with capping and turbid secretions. Further towards the posterior tarsal area, dilated, engorged telangiectatic vessels were present. The marginal lid erythema extended not only to the tarsal plate, but also to the inferior bulbar conjunctiva. Tear break-up time was notably decreased and corneae revealed inferior, bilateral punctate epithelial erosions. A diagnosis of rosacea blepharoconjunctivitis was made.

The patient was given a topical gel of 1% PVP-I in a dimethylsulfoxide (DMSO) vehicle that was prepared from a licensed compounding pharmacy. The treatment was administered twice daily and delivered by rubbing the gel onto the lash line and eyelid. At the first follow up visit one week later, remarkable improvements were noted. Most prominently, much of the conjunctivitis, anterior lid erythema and thickening had reversed. The patient was instructed to decrease the gel to once daily, but continue treatment for a total of one month. At this second follow up visit, not only were the initial improvements conserved, but the posterior lid margin vessels and telangiectasia had begun to attenuate and involute. Moreover, meibomian capping was no longer present and secretions were less viscous. Besides occasional mild tingling at the application site, the patient reported no other adverse effects Example 4

Demodex Blepharitis; Treated with 1.0% PVP-I in 40% USP Grade DMSO with Petrolatum This patient was suffering from anterior Demodex blepharitis. In this type of blepharitis, the anterior lid margin demonstrates madarosis, collarettes in cylindrical pattern and lash debris. Decreased tear break up time is also evident. The posterior lid margin may also be erythematous and demonstrate meibomian inspissation, fat saponification, and bacterial overgrowth. In this patient the condition had persisted for over 7 years and taken a chronic course. The patient had tried numerous antibiotics, steroids, tea tree oils, lid scrubs omega 3 fatty acids and anti-inflammatories without benefit. Cilia were epilated and examined under the microscope positively identifying Demodex folliculorum. Prepared was a composition as disclosed herein using 1.0% PVP-I in 40% DMSO with petrolatum. The patient was treated by applying the solution topically to the eyelid and conjunctiva twice daily. Within one week, improvement was noted in and around the eyelid. After two weeks the condition rapidly improved, as the conjunctival erythema abated, tear break up time and dry eye symptoms were normalized. Posterior lid margin demonstrated normal meibomian secretions. Microscopic assessment of cilia was negative for Demodex mites.

Example 5

Blepharoconjunctivitis; Treated with 0.3% PVP-I in 33% USP Grade DMSO with Glycerin This patient was suffering from blepharoconjunctivits. In this type of ocular inflammation, the anterior lid margin demonstrates madarosis, collarettes, scurf, lash debris and bacterial overgrowth. The posterior lid margin may also be erythematous, and demonstrate meibomian inspissation, capping, and keratinization. A hallmark of this process is abundant conjunctival injection which is secondary to anterior and posterior lid inflammation. In this patient the condition had persisted for over 1 week with an acute course. The patient had tried numerous antibiotics, steroids, lid scrubs, omega 3 fatty acids, and anti-inflammatories without benefit. Prepared was a composition as disclosed, herein using 0.3% PVP-I in 33% DMSO with glycerin. The patient was treated by applying the solution topically to the eyelid and conjunctiva twice daily. Within one week, improvement was noted in and around the eyelid. After two weeks the condition rapidly improved, as tear break up time and dry eye symptoms normalized. Close inspection of the anterior lid eyelid margin revealed healthy cilia without associated debris or bacterial overgrowth. Posterior lid margin inspection revealed healthy meibomian secretions and decreased lid erythema. The conjunctival examination revealed quiet and healthy tissue without inflammation.

Example 6

Adenoviral conjunctivitis; Treated with 0.5% PVP-I in 44% USP Grade DMSO with 3% Hydroxyethylcellulose This patient was suffering from adenoviral conjunctivitis. This common type of conjunctivitis follows a recent viral upper repiratory infection or contact with another infected person. Pre-auricular adenopathy is often present. In this patient, the conjunctiva demonstrated diffuse injection with chemosis. There was frequent clear ocular discharge present. Eyelid eversion revealed 3+ folliculareaction with few scattered petechiae. RPS Adenodetector sampling identified the causative agent to be an Adenovirus serotype. The patient had tried numerous antibiotics, steroids, lid scrubs and anti-inflammatories without benefit. Prepared was a composition as disclosed herein using 0.5% PVP-I in 44% DMSO with hydroxyethylaulose 3%. The patient was treated by applying the gel topically to the eyelid and conjunctiva three times daily. Within one week, improvement was noted in and around the eyelid evidenced by decreased chemosis and lid edema. At two weeks the condition was resolved, as the conjunctival erythema, discharge and follicles were no longer present. There was no development of corneal infiltrates or pseudomembranes.

Example 7

Epidemic Adenoviral conjunctivitis; Treated with 0.5% PVP-I in 41.5% % USP Grade DMSO with 3% Hydroxyethyl Cellulose This patient was suffering from epidemic adenoviral conjunctivitis. This type of conjunctivitis follows a recent viral upper repiratory infection or contact with another infected person. Pre-auricular adenopathy is often present. In this patient, the conjunctiva demonstrated diffuse injection with chemosis along with pseudomembrane formation. There was frequent clear ocular discharge present. Eyelid eversion revealed 3+ follicular reaction with few scattered petechiae. Corneal examination showed multifocal, sub-epithelial infiltrates, RPS Adenodetector sampling identified the causative agent to be an Adenovirus serotype. The patient had tried numerous antibiotics, steroids, lid scrubs and anti-inflammatories without benefit. Prepared was a composition as disclosed herein using 0.5% PVP-I in 41.5% DMSO with 3% hydroxyethyl cellulose. The patient was treated by applying the gel topically to the eyelid and conjunctiva three times daily. Within one week, improvement was noted in and around the eyelid. At two weeks the condition was resolved, as the conjunctival erythema, discharge, follicles and pseudomembranes were no longer present. The corneal infiltrates had also resolved and the cornea was clear and compact.

Example 8

Bacterial conjunctivitis; Treated with 0.25% PVP-I in 44% USP Grade DMSO with Hydroxyethylcellulose 3%

This patient was suffering from bacterial conjunctivitis. In this type of conjunctivitis there is often bacterial overgrowth and infiltration of the conjunctival epithelial layers. In this patient, conjunctiva also demonstrated diffuse injection with chemosis along with inflammatory membrane formation.

There was frequent purulent ocular discharge present. Eyelid eversion revealed. 3+ inflamed palpebral conjunctiva with few petechiae. Conjuctival cultures identified the causative agent as *Staphylococcus Aureus*. The patient had tried numerous antibiotics, steroids, lid scrubs and anti-inflammatories without benefit. Prepared was a composition as disclosed herein using 0.25% PVP-I in 44% DMSO with hydroxyethylcellulose 3%. The patient was treated by applying the gel topically to the eyelid and conjunctiva three times daily. Within three days, improvement was noted in and around the eyelid. At one week the condition was resolved, as the conjunctival erythema, discharge, follicles and inflammatory membranes were no longer present.

Example 9

Herpes Simplex Virus epithelial keratitis; Treated with 1.0% PVP-I in 49% USP Grade DMSO with 2.5% Hydroxyethylcellulose This patient was suffering from herpes simplex virus epithelial keratitis. In this type of keratitis there is often active replicating virus present within epithelial dendrites. With immune system weakening, the virus reactivates in the sensory ganglia and descends to infect the cornea. It can often manifest as recurrent disease. In this patient, the conjunctiva demonstrated diffuse injection and the cornea showed staining epithelial ulcerations in serpentine or dentritic form with terminal bulbs. Millipore testing reveals herpes simplex virus as the causative agent. The patient had tried numerous antibiotics, steroids, oral and topical anti-virals and anti-inflammatories without benefit. Prepared was a composition as disclosed herein using 1.0% PVP-I in 49% DMSO with 2.5% hydroxyethylcellulose. The patient was treated by applying the solution topically to the eye three times daily. Within three days, improvement was noted in and around the eye. The dendrites began to re-epithelialize and active virus replication was halted. At one week the condition was resolved and there was no evidence of the previous corneal lesions. The conjunctiva was white and quiet.

Example 10

Herpes Simplex Virus stromal keratitis; Treated with aqueous 0.15% PVP-I in 35% USP Grade DMSO with 3% Hydroxyethyl Cellulose This patient was suffering from herpes simplex virus stromal keratitis. In this type of keratitis there is often immune activation of the host secondary to molecular mimicry causing stromal corneal swelling. There may or may not be active replicating virus. It can often manifest as recurrent disease. In this patient, the conjunctiva demonstrated diffuse injection and the cornea showed diffuse corneal swelling with opacification. The patient had tried numerous antibiotics, steroids, oral and topical anti-virals and anti-inflammatories without benefit. Prepared was a composition as disclosed herein using 0.15% PVP-I in 35% DMSO with hydroxyethyl cellulose 3%. The patient was treated by applying the solution gel to the eye three times daily. Within three days, improvement was noted in and around the eye. The stromal edema began to clear and the patient was without any staining dendrites. At one week the condition was resolved and there was no evidence of the previous corneal lesions, cicatrization, or neovascularization. The conjunctiva was white and quiet.

Example 11

Herpes Simplex Virus Endothelial Keratitis; Treated with Aqueous 0.5% PVP-I in 48% USP Grade DMSO with 3% Hydroxyethyl Cellulose This patient was suffering from herpes simplex virus endothelial keratitis. In this type of keratitis there is often immune activation of the host secondary to molecular mimicry directed at endothelial cells. There may or may not be active replicating virus. It can often manifest as recurrent disease. In this patient, the conjunctiva demonstrated diffuse injection and the cornea showed disciform endothelial inflammation with keratic precipitates. Some stromal corneal edema was also present. The anterior chamber revealed rare inflammatory cells and mild trabeculitis. The patient had tried numerous antibiotics, steroids, oral and topical anti-virals and anti-inflammatories without benefit. Prepared was a composition as disclosed herein using 0.5% PVP-I in 48% DMSO with 3% hydroxyethyl cellulose. The patient was treated by applying the gel topically to the eye three times daily. Within three days, improvement was noted in and around the eye. The stromal edema began to clear and the keratic precipitates attenuated. The anterior chamber cell and flare was no longer present. At one week the condition was resolved and there was no evidence of the previous corneal swelling. There was no residual corneal cicatrization, or neovascularization. The conjunctiva was white and quiet.

Example 12

Hepres Zoster Ophthalmicus; Treated with Aqueous 1.8% PVP-I in 40% USP Grade DMSO with Petralatum This patient was suffering from herpes zoster virus epithelial keratitis. In this type of keratitis there is often viral infection within the eye along with erythematous macules and excoriations in dermatomal distribution. With immune system weakening, the herpes zoster virus is reactivated within the ophthalmic division of the trigeminal nerve. In this patient, the conjunctiva demonstrated diffuse injection and the cornea showed rose bengal staining epithelial "stuck on" dendrites in without terminal bulbs. The underlying corneal stroma demonstrated central edema without keratic precipitates. Fundus examination was negative for vasculitis. The patient had tried numerous antibiotics, steroids, oral and topical anti-virals and anti-inflammatories without benefit. Prepared was a composition as disclosed herein using 1.8% PVP-I in 40% DMSO with petralatum. The patient was treated by applying the solution topically to the eye three times daily. Within three days, improvement was noted in and around the eye. The dendrites began to re-epithelialize and active virus replication was halted. At one week the condition was resolved and there was no evidence of the previous corneal lesions. The conjunctiva was white and quiet and the cornea was clear and compact.

Example 13

Gram Positive Bacterial Corneal Ulceration; Treated with Aqueous 0.35% PVP-I in 45% USP Grade DMSO with 3% Hydroxyethylcellulose This patient was suffering from a bacterial corneal ulceration. In this type of infection there is often a history of contact lens use, however, this is not a prerequisite. Bacteria is introduced into the eye through a small break in the epithelium and gains foothold to the underlying structures. In this patient, the conjunctiva demonstrated diffuse injection with pyogenic discharge. The cornea demonstrated a central, three-millimeter circular infiltrate with overlying central epithelial defect. The infiltrate induced stromalysis and the resultant cornea had thinned by approximately thirty percent. There was a one millimeter layered hypopyon in the anterior chamber. Corneal cultures were taken, and Coagulase-negative Streptococcal species were identified. The patient had tried numerous antibiotics, steroids, oral and topical anti-virals and anti-inflammatories without benefit. Prepared was a composition as disclosed herein using aqueous 0.35% PVP-I in 45% DMSO with 3% hydroxyethylcellulose. The patient was treated by applying the solution topically to the eye six times daily. Within three days, improvement was noted in and around the eye. The corneal melt had halted and re-epithelialization had taken place. At one week the hypopyon had resolved, the conjunctiva cleared and a small central infiltrate remained. By week two, the patient was healed and no active bacterial infection remained. A central corneal cicatrix was evident in the area of previous active infiltrate.

Example 14

Gram Negative Bacterial Corneal Ulceration; Treated with Aqueous 0.2% PVP-I in 36% USP Grade DMSO with 3% Hydroxyethylcellulose This patient was suffering from a bacterial conical ulceration. In this type of infection there is often a history of contact lens use, however, this is not a prerequisite. Bacteria is introduced into the eye through a small break in the epithelium and gains foothold to the underlying structures. In this patient, the conjunctiva demonstrated diffuse injection with pyogenic discharge. The cornea demonstrated a central, five-millimeter circular infiltrate with overlying central epithelial defect. The infiltrate had induced abundant stromalysis and the resultant cornea had thinned by approximately seventy-five percent. There was a two millimeter layered hypopyon in the anterior chamber. Corneal cultures were taken, and Pseudomonas aeruginosa species was identified. The patient had tried numerous antibiotics, steroids, oral and topical anti-virals and anti-inflammatories without benefit. Prepared was a composition as disclosed herein using 0.2% PVP-I in 36% DMSO with 3% hydroxyethylcellulose. The patient was treated by applying the solution topically to the eye six times daily. Within three days, improvement was noted in and around the eye. The corneal melt had halted and re-epithelialization had taken place. At one week the hypopyon had resolved, the conjunctiva cleared and a small central infiltrate remained. By week two, the patient was healed and no active bacterial infection remained. A central corneal cicatrix was evident in the area of previous active infiltrate.

Example 15

Fungal Corneal Ulceration; Treated with Aqueous 1.2% PVP-I in 45% USP Grade DMSO with 3% Hydroxyethylcellulose This patient was suffering from a fungal corneal ulceration. In this type of infection there is often a history of contact lens use, however, this is not a prerequisite. Fungus is introduced into the eye through a small break in the epithelium and gains foothold to the underlying structures. In this patient, the conjunctiva demonstrated diffuse injection with pyogenic discharge. The cornea contained multifocal, feather-like infiltrates with overlying central epithelial defect. The infiltrates had induced minimal stromalysis and the resultant cornea was not thinned. There was no hypopyon, however, cell and flare were present. Corneal cultures were taken, and Fusarium species was identified. The patient had tried numerous antifungals, antibiotics, steroids, oral and topical anti-virals and anti-inflammatories without benefit. Prepared was a composition as disclosed herein using 1.2% PVP-I in 45% DMSO with 3% hydroxyethylcellulose. The patient was treated by applying the solution topically to the eye six times daily. Within one week, improvement was noted in and around the eye. The cornea had begun the process of re-epithelialization. At two weeks, corneal infiltrate was resolved, the conjunctiva had cleared and the anterior chamber was quiet. A central corneal cicatrix was evident in the area of previous active infiltrate.

Example 16

Acanthamoeba Corneal Ulceration; Treated with Aqueous 0.4% PVP-I in 39% USP Grade DMSO with Hydroxyethyl Cellulose This patient was suffering from an Acanthamoeba corneal ulceration. In this type of infection there is often a history of contact lens use and home-made contact lens solutions, however, this is not a prerequisite. Acanthamoeba parasites are often introduced into the eye through a small break in the epithelium and gains foothold to the underlying structures. The patient endorses pain out of proportion with examination. In this patient, the conjunctiva demonstrated diffuse injection. The cornea contained multiple bullous lesions with enlarged corneal nerves. There was an overlying epithelial defect and faint ring-shaped infiltrate. The infiltrate had induced minimal stromalysis and the resultant cornea was not thinned. There was no hypopyon, however, cell and flare were present. Corneal cultures were taken, and Acanthamoeba species were identified on non-nutrient agar with *E. coli* overlay. The patient had tried numerous anti-amoeboid medicines including chlorhexidine, propamidine, antifungals, antibiotics, steroids, oral and topical anti-virals and anti-inflarr oratories without benefit. Prepared was a composition as disclosed herein using 0.4% PVP-I in 39% DMSO with hydroxyethyl cellulose. The patient was treated by applying the solution topically to the eye six times daily. Within one week, improvement was noted in and around the eye. The corneal had begun the process of re-epithelialization and the ring ulcer began to lessen in intensity. At two weeks the corneal infiltrate was resolved, the conjunctiva cleared and perineuralgia abated. A central corneal cicatrix was evident in the area of previous active infiltrate.

Example 17

Conjunctival Squamous Papilloma; Treated with 1.9% PVP-I in 46% USP Grade DMSO with 3% Hydroxyethylcellulose This patient was suffering ftom a conjunctival papilloma. In this type of dysplasia conjunctival cells demonstrate an exophytic or cauliflower-like pattern. They may also grow in a finger-like pattern and are often lobulated with vascular cores. The process is often associated with UV exposure, smoking, or human papilloma virus. In this patient, the conjunctiva demonstrated an exophytic mass with a pedunculated base, frond-like growth and vascular core. Conjunctival biopsy was taken and pathology report confirmed the diagnosis. The patient had tried numerous topical chemotherapeutic agents such as mitomycin and interferon. Topical anti-inflammatories were also administered. Eventual excision with cryotherapy was performed, however, the lesion recurred. Prepared was a composition as disclosed herein using 1.9% PVP-I in 46% DMSO with 3% hydroxyethylcellulose. The patient was treated by applying the solution topically to the eye four times daily. Within one month, improvement was noted in the eye. The conjunctival lesion had begun to involute and diminish surface area. At two months there had been complete regression of the lesion with healthy appearing underlying conjunctiva. Post-treatment biopsy in the affected area was negative.

Example 18

Corneal Squamous Papilloma; Treated with 0.8 PVP-I in 43% USP Grade DMSO 3% Hydroxyethylcellulose This patient was suffering from a corneal squamous papilloma. In this type of dysplasia corneal cells demonstrate an exophytic or cauliflower-like pattern. They may also grow in a finger-like pattern and are often lobulated with vascular cores. The process is often associated with UV exposure, smoking, or human papilloma virus. In this patient, the cornea demonstrated an exophytic mass with a pedunculated base, frond-like growth and vascularCorneal biopsy was taken and pathology report confirmed the diagnosis. The patient had tried numerous topical chemotherapeutic agents such as mitomycin and interferon. Topical anti-inflammatories were also administered. Eventual excision with cryotherapy was performed, however, the lesion recurred. Prepared was a composition as disclosed herein using 0.8% PVP-I in 43% DMSO with 3% hydroxyethylcellulose. The patient was treated by applying the solution opically to the eye four times daily. Within one month, improvement was noted in the eye. The corneal lesion had begun to involute and diminish in surface area. At two months there had been complete regression of the lesion with healthy appearing corneal tissue. Post-treatment biopsy in the affected area was negative.

Example 19

Eyelid Squamous Papilloma; Treated with 1.7% PVP-I in 47% USP Grade DMSO with 3% Hydroxyethylcellulose This patient was suffering from an eyelid squamous papilloma. In this type of dysplasia, cells demonstrate an exophytic or cauliflower-like pattern. They may also grow in a finger-like pattern and are often lobulated with vascular cores. The process is often associated with UV exposure, smoking, or human papilloma virus. In this patient, the eyelid lamellae demonstrated an exophytic mass with a pedunculated base, frond-like growth and vascular core. Eyelid biopsy was taken and pathology report confirmed the diagnosis. The patient had tried numerous topical chemotherapeutic agents such as mitomycin and interferon. Topical anti-inflammatories were also administered. Eventual excision with cryotherapy was performed, however, the lesion recurred. Prepared was a composition as disclosed herein using 1.7% PVP-I in 47% DMSO with 3% hydroxyethylcellulose. The patient was treated by applying the solution topically to the eye four times daily. Within one month, improvement was noted. The eyelid lesion had begun to involute and diminish in surface area. At two months there had been complete regression of the lesion with healthy appearing eyelid tissues and structures.

Example 20

Eyelid Verrucae; Treated with 0.1% PVP-I in 43% USP Grade DMSO 3% Hydroxyethylcellulose This patient was suffering from eyelid verrucae. This type of eyelid growth usually commences with gray or tan papules that progress to hyperkeratotic lesions with a papillomatous surface. The process is often associated with human papilloma virus infection of the epithelial layers. In this patient, the superior eyelid demonstrated a solid white growth with a papillomatous surface. Eyelid biopsy was taken and pathology report confirmed the diagnosis. The patient had tried numerous topical agents without benefit. Cryotherapy was eventually performed, however, the lesion recurred. Prepared was a composition as disclosed herein using 0.1% PVP-I in 43% DMSO with polypropylene glycol. The patient was treated by applying the solution topically to the eyelid structures four times daily. Within two weeks, improvement was noted. The lesion had begun to involute and diminish in surface area. At one month there had been complete regression of the lesion with healthy appearing eyelid tissues and skin.

Example 21

Eyelid Molluscum Contagiosum; Treated with 9% PVP-I in 39% USP Grade DMSO with 3% Hydroxyethylcellulose This patient was suffering from an eyelid associated molluscum contagiosum. This type of eyelid infection usually demonstrates flesh colored, dome-shaped pearly papules with dimpled centers. The process is often associated with pox virus infection of the epithelial layers. In this patient, the upper eyelid and lid margin demonstrated multiple flesh colored papules with dimpled centers. The patient had tried numerous topical agents without benefit including salicylic acid and imiquimod. Cryotherapy with excision was eventually performed, however, the lesions recurred. Prepared was a composition as disclosed herein using 0.9% PVP-I in 39% DMSO with hydroxyethyl cellulose. The patient was treated by applying the solution topically to the eyelid and margin structures four times daily. Within two weeks, improvement was noted. The lesions had begun to involute and diminish in surface area. At one month there had been complete regression of the lesions with healthy appearing eyelid tissues and lamellae.

Example 22

Eyelid Antisepsis Prior to Cataract Surgery; Treated with 0.2% PVP-I in 44% USP Grade DMSO 3% Hydroxyethylcellulose This patient was suffering from an anterior and posterior blepharitis prior to cataract surgery. Numerous ophthalmic studies have implicated bacteria that populate the eyelids and conjunctiva as those being responsible for post-operative infectious endophthalmitis. It is therefore routine to attempt to sterilize these surfaces prior to commencing said procedure. In this patient, the posterior lid margin demonstrated meibomian gland thickening, keratinization, fat saponification, and dilated, telangectatic lid vessels. The anterior lid margin also demonstrated scurf and bacterial overgrowth. The patient had tried numerous topical agents to sterilize the ocular surface including topical antibiotics and antiseptics without benefit. Prepared was a composition as disclosed herein using 0.2% PVP-I in 44% DMSO with 3% hydroxyethylcellulose The patient was treated by applying the solution topically to the eye and eyelid three times daily commencing 3 days prior to the procedure. On the day of the procedure, conjunctival cultures were taken and demonstrated no growth. The patient underwent a successful procedure and had an uneventful post-operative course.

Example 23

Eyelid Antisepsis Prior to Intravitreal Injection; Treated with 1.4% PVP-I in 32% USP Grade DMSO with 3% Hydroxyethylcellulose This patient was suffering from an anterior and posterior blepharitis prior to intravitreal injection. Numerous ophthalmic studies have implicated bacteria that populate the eyelids and conjunctiva as those being responsible for postinjection infectious endophthalmitis. It is therefore routine to attempt to sterilize these surfaces prior to commencing said procedure. In this patient, the posterior lid margin demonstrated meibomian gland thickening, keratinization, fat saponification, and dilated, telangectatic lid vessels. The anterior lid margin also demonstrated scurf and bacterial overgrowth. The patient had tried numerous topical agents to sterilize the ocular surface including topical antibiotics and antiseptics without benefit. Prepared was a composition as disclosed herein using 1.4% PVP-I in 32% DMSO with 3% hydroxyethylcellulose. The patient was treated by applying the solution topically to the eye and eyelid three times daily commencing 3 days prior to the procedure. On the day of the procedure, conjunctival cultures were taken and demonstrated no growth. The patient underwent a successful injection and had an uneventful post-operative course.

The Examples and description provided herein are not intended as, and are not, limiting to the breadth of protection afforded within the full scope and spirit of the invention as described.

The invention claimed is:

1. A stable ophthalmically acceptable gel composition comprising
   0.15% to 1.5% povidone-iodine (PVP-I);
   30% to 97% dimethyl sulfoxide (DMSO);
   2.0% to 5% gelling agent selected from the group consisting of hydroxypropyl methylcellulose, hydroxymethyl cellulose, and hydroxyethyl cellulose; and
   water or isotonic co-solvent
   wherein, the composition is a topical ophthalmic gel, free of additional anti-inflammatory drug.

2. The composition of claim 1, comprising 0.15% to 1.0% PVP-I.

3. The composition of claim 1, comprising 0.25% to 0.5% PVP-I.

4. The composition of claim 1, comprising about 0.25% PVP-I.

5. The composition of claim 1, comprising 30% to 70% DMSO.

6. The composition of claim 1, comprising 40% to 49% DMSO.

7. The composition of claim 1, comprising 44% DMSO.

8. The composition of claim 1, comprising 2% to 3% gelling agent.

9. The composition of claim 1 comprising 3% gelling agent.

10. The composition of claim 1, comprising:
    0.25% PVP-I;
    44% DMSO;
    2% hydroxymethyl cellulose; and
    the isotonic co-solvent, and
    wherein said composition is steroid-free and NSAID-free.

11. A stable gel composition of claim 1, wherein, the composition is a topical ophthalmic preparation wherein each ingredient is ophthalmically acceptable, and
    said ophthalmic gel composition retains at least 85% of titratable iodine in povidone-iodine starting material for at least 72 hours.

12. The stable gel composition of claim 11 wherein the composition retains at least 85% of titratable iodine in povidone-iodine starting material for at least one month.

13. The stable gel composition of claim 11 wherein the composition retains at least 85% of titratable iodine in povidone-iodine starting material for up to 12 months.

14. A method of treating an infectious condition of the eye or eyelid, said method comprising the step of:
    applying an effective amount of a stable, topical ophthalmic gel composition of claim 1 to a site of the infection as needed to reduce or eliminate the infection.

15. The method of claim 14 wherein said infectious condition is selected from the group consisting of blepharitis, conjunctivitis, corneal ulcer, bacterial keratitis, viral keratitis, post-operative endophthalmitis, and endophthalmitis after intravitreal or intracameral injection.

16. The method of claim 15, wherein the infectious condition is caused by or associated with one or more infectious agents selected from the group consisting of bacteria, demodex, fungus or yeast, and virus.

17. The method of claim 14 wherein the condition is blepharitis, blepharoconjunctivitis, conjunctivitis, keratitis or infectious corneal ulcer.

18. The method of claim 14, wherein the infectious agent is a virus.

19. The method of clam 14, wherein the infectious agent is demodex.

* * * * *